(12) United States Patent
Simon

(10) Patent No.: US 8,142,774 B2
(45) Date of Patent: *Mar. 27, 2012

(54) METHODS OF TREATMENT USING ELECTROMAGNETIC FIELD STIMULATED STEM CELLS

(75) Inventor: Bruce Simon, Mountain Lakes, NJ (US)

(73) Assignee: EBI, LLC, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/791,333

(22) Filed: Jun. 1, 2010

(65) Prior Publication Data

US 2010/0239544 A1 Sep. 23, 2010

Related U.S. Application Data

(63) Continuation of application No. 11/268,696, filed on Nov. 7, 2005, now Pat. No. 7,744,869, which is a continuation-in-part of application No. 10/924,241, filed on Aug. 20, 2004, now abandoned.

(60) Provisional application No. 60/496,526, filed on Aug. 20, 2003.

(51) Int. Cl.
*A01N 63/00* (2006.01)
*A01N 65/00* (2009.01)
*C12N 5/00* (2006.01)
*C12N 5/02* (2006.01)

(52) U.S. Cl. ............... 424/93.7; 424/93.1; 435/325
(58) Field of Classification Search ............... 424/93.7, 424/93.1; 435/325
See application file for complete search history.

(56) References Cited

U.S. PATENT DOCUMENTS

| | | | |
|---|---|---|---|
| 3,871,961 A | 3/1975 | Gianessi |
| 4,467,809 A | 8/1984 | Brighton |
| 4,846,181 A | 7/1989 | Miller |
| 5,032,508 A | 7/1991 | Naughton et al. |
| 5,197,985 A | 3/1993 | Caplan et al. |
| 5,226,914 A | 7/1993 | Caplan et al. |
| 5,292,252 A | 3/1994 | Nickerson et al. |
| 5,312,439 A | 5/1994 | Loeb |
| 5,338,286 A | 8/1994 | Abbott et al. |
| 5,429,938 A | 7/1995 | Humes |
| 5,486,359 A | 1/1996 | Caplan et al. |
| 5,723,331 A | 3/1998 | Tubo et al. |
| 5,811,094 A | 9/1998 | Caplan et al. |
| 5,820,918 A | 10/1998 | Ronan et al. |
| 5,843,766 A | 12/1998 | Applegate et al. |
| 5,919,679 A | 7/1999 | Blackman et al. |
| 6,030,635 A | 2/2000 | Gertzman et al. |
| 6,190,893 B1 | 2/2001 | Shastri et al. |
| 6,214,369 B1 | 4/2001 | Grande et al. |
| 6,235,251 B1 | 5/2001 | Davidson |
| 6,287,340 B1 | 9/2001 | Altman |
| 6,291,240 B1 | 9/2001 | Mansbridge et al. |
| 6,323,146 B1 | 11/2001 | Pugh et al. |
| 6,353,763 B1 | 3/2002 | George et al. |
| 6,355,239 B1 | 3/2002 | Bruder et al. |
| 6,387,367 B1 | 5/2002 | Davis-Sproul et al. |
| 6,454,787 B1 | 9/2002 | Maddalo et al. |
| 6,485,963 B1 | 11/2002 | Wolf et al. |
| 6,535,767 B1 | 3/2003 | Kronberg |
| 6,541,024 B1 | 4/2003 | Kadiyala et al. |
| 6,569,654 B2 | 5/2003 | Shastri et al. |
| 6,585,992 B2 | 7/2003 | Pugh et al. |
| 6,605,275 B1 | 8/2003 | Boyse et al. |
| 6,652,473 B2 | 11/2003 | Kaufman et al. |
| 6,673,597 B2 | 1/2004 | Wolf et al. |
| 6,673,603 B2 | 1/2004 | Baetge et al. |
| 6,777,231 B1 | 8/2004 | Katz et al. |
| 6,875,442 B2 | 4/2005 | Holy et al. |
| 6,955,642 B1 | 10/2005 | Simon |
| 6,995,013 B2 | 2/2006 | Connelly et al. |
| 7,226,587 B2 | 6/2007 | Clancy et al. |
| 7,410,497 B2 | 8/2008 | Hastings et al. |
| 7,744,869 B2 | 6/2010 | Simon |
| 7,840,272 B2 | 11/2010 | Kronberg et al. |
| 7,887,843 B2 | 2/2011 | Libera et al. |
| 2002/0115208 A1 | 8/2002 | Mitchell et al. |
| 2004/0005297 A1 | 1/2004 | Connelly et al. |
| 2004/0131601 A1 | 7/2004 | Epstein et al. |
| 2004/0267333 A1 | 12/2004 | Kronberg |
| 2005/0049640 A1 | 3/2005 | Gurtner et al. |
| 2005/0074477 A1 | 4/2005 | Josimovic-Alasevic et al. |
| 2005/0084962 A1 | 4/2005 | Simon |

(Continued)

FOREIGN PATENT DOCUMENTS

WO WO 99/22747 5/1999

(Continued)

OTHER PUBLICATIONS

Luo et al. Genes and Development, 9: 2808-2820, 1995.*

(Continued)

*Primary Examiner* — Thaian N Ton
(74) *Attorney, Agent, or Firm* — Harness, Dickey

(57) ABSTRACT

Methods of modifying stem cells and compositions of modified stem cells, in particular mesenchymal stem cells, using electric or electromagnetic fields. In various embodiments, the present invention's methods are for the treatment of a human or other mammal subject in need thereof, comprising providing an in vitro culture comprising mesenchymal stem cells, administering an electric stimulation to the in vitro culture, and implanting the mesenchymal stem cells into the subject. Methods also include treatment of a human or other mammal subject, comprising implanting mesenchymal stem cells into the subject, and administering an electric stimulation to the mesenchymal stem cells in situ. Other embodiments include methods of administering electric stimulation in conjunction with growth factors to stem cells.

5 Claims, No Drawings

U.S. PATENT DOCUMENTS

| | | | |
|---|---|---|---|
| 2005/0112759 | A1 | 5/2005 | Radisic et al. |
| 2005/0205498 | A1 | 9/2005 | Sowemimo-Coker et al. |
| 2006/0057693 | A1 | 3/2006 | Simon |
| 2006/0094112 | A1 | 5/2006 | Babalola et al. |
| 2006/0293724 | A1 | 12/2006 | Kronberg et al. |
| 2008/0039901 | A1 | 2/2008 | Kronberg et al. |

FOREIGN PATENT DOCUMENTS

| | | |
|---|---|---|
| WO | WO 01/68811 | 9/2001 |
| WO | WO 02/10351 | 2/2002 |

OTHER PUBLICATIONS

Masuda et al. The Prostate, 59: 101-106, 2004.*

Pepper et al. J. of Orthopaedic Res., 14: 296-302, 1996.*

Hartig et al. Eur. Biophys. J., 29: 499-506, 2000.*

Colter, D. et al. "Identification of a Subpopulation of Rapidly Self-Renewing and Multipotential Adult Stem Cells in Colonies of Human Marrow Stromal Cells" PNAS, vol. 98, No. 14 (pp. 7841-7845) Jul. 3, 2001.

"Stem Cell Basics", National Institutes of Health, http://stemcells.nih.gov/info/basics/basics4.asp (6 pages).

"Stem Cells: A Primer", National Institutes of Health, http://www.nih.gov/news/stemcell/primer.htm, Sep. 2002 (17 pages).

"Use of Electrical and Magnetic Stimulation in Orthopedics and Traumatology", Consensus Conference, Bologna, Jun. 11, 1997 (27 pages).

Aaron et al., "Acceleration of Experimental Endochondral Ossification by Biophysical Stimulation of the Progenitor Cell Pool", Journal of Orthopaedic Research, vol. 14, No. 4, 1996, pp. 582-589.

Aaron et al., "Power Frequency Fields Promote Cell Differentiation Coincident With an Increase in Transforming Growth Factor-β1 Expression", Bioelectromagnetics, vol. 20, 1999, pp. 453-458.

Aaron et al., "Stimulation of Experimental Endochondral Ossification by Low-Energy Pulsing Electromagnetic Fields", Journal of Bone and Mineral Research, vol. 4, No. 2, 1989, pp. 2271-233.

Aaron et al., "Therapeutic Effects of Electromagnetic Fields in the Stimulation of Connective Tissue Repair", Journal of Cellular Biochemistry, vol. 52, 1993, pp. 42-46.

Aaron et al., "Upregulation of basal TG9β1 levels by EMF coincident with chondrogenesis—implications for skeletal repair and tissue engineering", Journal of Orthopaedic Research, vol. 20, 2002, pp. 233-240.

Binderman et al., "Stimulation of skeletal-derived cell cultures by different electric field intensities is cell-specific", Biochimica et Biophysica Acta, vol. 844, 1985, pp. 273-279.

Bozic et al., "In Vivo Evaluation of Coralline Hydroxyapatite and Direct Current Electrical Stimulation in Lumbar Spinal Fusion", SPINE, vol. 24, No. 20, 1999, pp. 2127-2133.

Brain et al., "Childhood Leukemia: Electric and Magnetic Fields as Possible Risk Factors", Environmental Health Perspectives, vol. 111, No. 7, Jun. 2003, pp. 962-970.

Celil, A. et al. "BMP-2 and Insulin-like Growth Factor-I Mediate Osterix (Osx) Expression in Human Mesenchymal Stem Cells via the MAPK and Protein Kinase D Signaling Pathways" The Journal of Biological Chemistry, vol. 280, No. 36 (pp. 31353-31359) Sep. 2005.

Ciombor et al., "Influence of Electromagnetic Fields on Endochondral Bone Formation", Journal of Cellular Biochemistry, vol. 52, 1993, pp. 37-41.

Ciombor et al., "Low frequency EMF regulates chondrocyte differentiation and expression of matrix proteins", Journal of Orthopaedic Research, vol. 20, 2002, pp. 40-50.

Duran et al., Pulsed Electromagnetic Fields Enhance BMP-2 Induced Differentiation of Mesenchymal Stem Cells to Osteoblasts, Abstract from Mar. 19-22, 2006 Orthopaedic Research Society Meeting (1page).

Eppich et al., "Pulsed electric fields for selection of hematopoietic cells and depletion of tumor cell contaminants", Nature Biotechnology, vol. 18, Aug. 2000, pp. 882-887.

Fodor, W. "Tissue engineering and cell based therapies, from the bench to the clinic: The potential to replace, repair and regenerate".

France et al., "The Efficacy of Direct Current Stimulation for Lumbar Intertransverse Process Fusions in an Animal Model", SPINE, vol. 26, No. 9, 2001, pp. 1002-1007.

Fredericks, D. et al. "Effects of Pulsed Electromagnetic Fields on Bone Healing in a Rabbit Tibial Osteotomy Model" Journal of Orthopaedic Trauma, vol. 14, No. 2 (pp. 93-100) 2000.

Hatada et al., "Gene correction in hematopoietic progenitor cells by homologous recombination", PNAS, vol. 97, No. 25, Dec. 5, 2000, pp. 13807-13811.

Hua, W. et al. "Effect of Electromagnetic Fields on Proliferation and Differentiation of Cultured Mouse Bone Marrow Mesenchymal Stem Cells" Journal of Huazhong University Science an Technology, 25(2) (pp. 185-187) 2005.

Leisner, S. et al. "The Effect of Short-duration, High-intensity Electromagnetic Pulses on Fresh Ulnar Fractures in Rats" J. Vet. Med. A., vol. 49 (pp. 33-37) 2002.

Lohmann et al., "Pulsed electromagnetic fields affect phenotype and connexin 43 protein expression in MLO-Y4 osteocyte-like cells and ROS 17/2.8 osteoblast-like cells", Journal of Orthopaedic, Research, vol. 21, 2003, pp. 326-334.

Midura, R. et al. "Pulsed electromagnetic field treatments enhance the healing of fibular osteotomies" Journal of Orthopaedic Research, vol. 23 (1035-1046) 2005.

Mironov, V. et al. "What is regenerative medicine? Emergence of applied stem cell and developmental biology" Expert Opin Biol Ther, vol. 4, No. 6 (pp. 773-781) 2004.

Nafziger et al., "Investigation of the Effects of 50 Hz Magnetic Fields on Purified Human Hematopoietic Progenitors", Life Sciences, vol. 61, No. 19, 1997, pp. 1935-1946.

Rawadi, G. et al. "BMP-2 Controls Alkaline Phosphatase Expression and Osteoblast Mineralization by a Wnt Autocrine Loop" Journal of Bone and Mineral Research, vol. 18, No. 10 (pp. 1842-1853) 2003.

Schwartz, Z. et al. "Pulsed Electromagnetic Fields Enhance BMP-2 Dependent Osteoblast Differentiation of Human Mesenchymal Stem Cells" Journal of Orthopaedic Research, publislhed online in Wiley InterScience, DOI 10.1002/jor.20591 (8 pages) 2008.

Takano-Yamamoto, T. et al. "Effect of a Pulsing Electromagnetic Field on Demineralized Bone-matrix-induced Bone Formation" J Dent Res, vol. 71, No. 12 (pp. 1920-1925) Dec. 1992.

Anderer, U. et al. "In Vitro Engineering of Human Autogenous Cartilage" Journal of Bone and Mineral Research, vol. 14, No. 8 (pp. 1420-1429) Aug. 2002.

Brittberg, M. et al. "Autologous Chondrocytes Used for Articular Cartilage Repair" Clinical Orthopaedics and Related Research, No. 391S (pp. S337-S348) Oct. 2001.

Brittberg, M. et al. "Treatment of Deep Cartilage Defects in the Knee with Autologous Chondrocyte Transplantation" The New England Journal of Medicine, vol. 331, No. 14 (pp. 889-895) Oct. 1994.

Carrier, R. et al. "Perfusion Improves Tissue Architecture of Engineered Cardiac Muscle" Tissue Engineering, vol. 8, No. 2 (pp. 175-188) Apr. 1, 2001.

Meyer, U. et al. "Mechanical Tension in Distraction Osteogenesis Regulates Chondrocytic Differentiation" International Journal of Oral and Maxillofacial Surgery, vol. 30, No. 6 (pp. 522-530) Dec. 2001.

Nishikori, T. et al. "Effects of Low-Intensity Pulsed Ultrasound on Proliferation and Chondroitin Sulfate Synthesis of Cultured Chondrocytes Embedded in Atelocollagen Gel" Journal of Biomedical Materials Research, vol. 59, No. 2 (pp. 201-206) Feb. 2002.

Ochi, M. "Current Concepts in Tissue Engineering Technique for Repair of Cartilage Defect" Artificial Organs, vol. 25, No. 3 (pp. 172-179) Mar. 2001.

Radisic, M. et al. "High-Density Seeding of Myocyte Cells for Cardiac Tissue Engineering" Biotechnology and Bioengineering, vol. 82, No. 4 (pp. 403-414) May 20, 2003.

Wiesmann, H. et al. "Extracorporal Biophysical Stimulation of Osteoblast Cultures for Bone Tissue Engineering" Tissue Engineering, vol. 9, No. 4 (Abstract Only) Aug. 2003.

* cited by examiner

METHODS OF TREATMENT USING ELECTROMAGNETIC FIELD STIMULATED STEM CELLS

This application is a continuation of U.S. patent application Ser. No. 11/268,696 filed Nov. 7, 2005 (issued Jun. 29, 2010 as U.S. Pat. No. 7,744,869), which is a continuation-in-part of U.S. patent application Ser. No. 10/924,241, filed Aug. 20, 2004, now abandoned which claims the benefit to U.S. Provisional Application No. 60/496,526, filed on Aug. 20, 2003.

INTRODUCTION

The present invention relates to methods and compositions for treating trauma, disease, or tissue disorders using, in various embodiments, stem cells.

One of the responses to a bodily trauma, disease, or disorder is the recruitment of pluripotent stem cells. Repair is effectuated by subsequent proliferation and differentiation of the stem cells into specific cells. For example, mesenchymal stem cells proliferate and differentiate into specific cells to repair damage to bone.

There are a number of complex steps or processes that are involved in bone remodeling and healing, including the proliferation of mesenchymal stem cells from the bone marrow, periosteum, and surrounding soft tissue. And, unlike most other tissues which heal when injured by forming connective tissue, bone heals by the formation of new bone. Bone is subject to constant breakdown and re-synthesis in a complex process mediated by osteoblasts, which produce new bone, and osteoclasts, which destroy bone. Osteoblasts arise when mesenchymal stem cells, located near all bony surfaces, differentiate under the influence of growth factors. These stem cells are transformed into osteoprogenitor cells by these locally produced bone morphogenetic proteins. Certain growth factors have been shown to have clinical benefit for treatment of bone defects, injury, disorders, or disease.

Stem cells can be obtained from embryonic or adult tissues of humans or other animals. Irrespective of tissue origin, all stem cells are originally unspecialized, are capable of dividing and renewal, and can give rise by differentiation to specialized cell types (see, e.g., National Institutes of Health, Stem Cell Basics, available on the internet at http://stemcells.nih.gov/infoCenter/StemCellBasics.asp). For example, mesenchymal stem cells, which are stem cells obtained from adult or embryonic connective tissues, can differentiate into many different cell types, such as, for example, bone, cartilage, fat, ligament, muscle and tendon.

The use of stem cells in certain therapeutic applications has been investigated. See, for example: U.S. Pat. No. 5,197,985, Caplan et al., issued Mar. 30, 1993; U.S. Pat. No. 5,226,914, Caplan et al., issued Mar. 30, 1993; U.S. Pat. No. 5,486,359, Caplan et al., issued Mar. 30, 1993; U.S. Pat. No. 5,811,094, Caplan et al., issued Sep. 22, 1998; U.S. Pat. No. 6,355,239, Bruder et al., issued Mar. 12, 2002; U.S. Pat. No. 6,387,367, Davis-Sproul et al., issued May 14, 2002; U.S. Pat. No. 6,541,024, Kadiyala et al., issued Apr. 1, 2003; and Eppich et al., *Nature Biotechnology* 18: 882-887, 2000. However, none of the above references describe exposure of stem cells in vitro to electromagnetic fields to beneficially modify the stem cells for therapeutic use, nor do they disclose implantation of stem cells to a mammalian recipient followed by in situ application of electric fields.

Therapies involving the alteration of cell or tissue properties by exposure to electromagnetic fields have been proposed. See, Aaron and Ciombor, *J. Cellular Biochemistry* 52: 42-46, 1993; Aaron et al., *J. Bone Miner. Res.* 4: 227-233, 1989; Aaron and Ciombor, *J. Orthop. Res.* 14: 582-589, 1996; Aaron et al., *Bioelectromagnetics* 20: 453-458, 1999; Aaron et al, *J. Orthop. Res.* 20: 233-240, 2000; Ciambor et al., *J. Orthop. Res.* 20: 40-50, 2000; U.S. Pat. No. 6,485,963, Wolf et al., issued Nov. 26, 2002; U.S. Pat. No. 5,292,252, Nickerson et al., issued Mar. 8, 1994; U.S. Pat. No. 6,235,251, Davidson, issued May 22, 2001; and Binderman et al., *Biochimica et Biophysica Acta* 844: 273-279, 1985. However, these references do not suggest treatment of mesenchymal stem cells with an electromagnetic field in vitro prior to transplantation to a mammalian recipient, nor do they describe implantation of mesenchymal stem cells to a recipient mammal followed by in situ exposure of the cells to an electromagnetic field.

SUMMARY

The present invention provides methods of modifying stem cells using electric or electromagnetic fields. In various embodiments, the present invention provides methods of increasing proliferation rate of mesenchymal stem cells by administering electric stimulation to mesenchymal stem cells in vitro. In other embodiments, the present invention provides methods of promoting differentiation of mesenchymal stem cells by administering electric stimulation to mesenchymal stem cells in vitro. In still other embodiments, the present invention provides methods for the treatment of a human or other mammal subject in need thereof, by providing an in vitro culture of mesenchymal stem cells, administering an electric stimulation to the in vitro culture, and implanting the mesenchymal stem cells into the subject. In various other embodiments, the present invention provides methods for the treatment of a human or other mammal subject in need thereof, by implanting mesenchymal stem cells into the subject, and administering an electric stimulation to the mesenchymal stem cells in situ. The present invention also provides compositions of mesenchymal stem cells treated with electric stimulation.

In addition, the present invention provides for various embodiments of the aforementioned methods of modifying stem cells, increasing proliferation of stem cells, promoting differentiation of stem cells, and methods of treatment using electric or electromagnetic fields, each in conjunction with the addition of growth factors. Likewise, the present invention also provides for various embodiments of the aforementioned compositions of stem cells with the addition of growth factors. And in various embodiments, the present invention provides for modulating mesenchymal stem cell activity using electrical stimulation plus the addition of growth factors where the result is more efficacious than either administering electrical stimulation or growth factors independently of one another.

The present invention affords benefits over those methods known in the art. Such benefits include one or more of: increased or accelerated stem cell proliferation; enhanced control of stem cell differentiation; enhanced maintenance of stem cell differentiation; enhanced ability for use of stem cells in tissue engineering applications; enhanced modulation of stem cell activity after implantation; the ability to effect tissue healing or growth without use of non-autologous growth factors; the ability to effect tissue growth using reduced levels of growth factors; increased rate of healing of tissue defects; and more complete healing of tissue defects. Further areas of applicability and advantages will become apparent from the following description. It should be understood that the description and specific examples, while exemplifying embodiments of the invention, are intended for purposes of illustration only and are not intended to limit the scope of the invention.

DESCRIPTION

The following definitions and non-limiting guidelines must be considered in reviewing the description of this invention set forth herein.

The headings (such as "Introduction" and "Summary,") and sub-headings (such as "Stem Cells") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations of the stated features. Specific examples are provided for illustrative purposes of how to make, use, and practice the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, devices, and methods of this invention.

The present invention involves the treatment of tissue defects in humans or other animal subjects. Specific materials to be used in the invention must, accordingly, be pharmaceutically acceptable. As used herein, such a "pharmaceutically acceptable" component is one that is suitable for use with humans and/or animals without undue adverse side effects (such as toxicity, irritation, and allergic response) commensurate with a reasonable benefit/risk ratio.

Stem Cells:

The compositions and methods of the present invention comprise and use stem cells. Preferably the stem cells are mammalian stem cells and preferably human stem cells. Stem cells can be derived from any tissue source, for example, cartilage, fat, bone tissue (such as bone marrow), ligament, muscle, synovia, tendon, umbilical cord (such as umbilical cord blood), and embryos. In a preferred embodiment, mesenchymal stem cells are used.

In various embodiments, the stem cells of the invention are mesenchymal stem cells. For example, the stem cells may be mesenchymal stem cells capable of differentiating into bone, cartilage, vasculature, blood cells, or nerve. Also, for example, the mesenchymal stem cells can be osteogenic stem cells, chondrogenic stem cells, angiogenic stem cells, or hematopoietic stem cells. In a preferred embodiment, the mesenchymal stem cells are embryonic or adult mesenchymal stem cells derived from embryonic or adult tissues, respectively, wherein "adult stem cells" include stem cells established from any post-embryonic tissue irrespective of donor age.

In other embodiments, the stem cells are autologous stem cells. In further embodiments, the stem cells are allogeneic stem cells. In still other embodiments, the stem cells are xenogeneic stem cells. Preferably, the stem cells are autologous stem cells or allogeneic stem cells. More preferably, the stem cells are autologous mesenchymal stem cells or allogeneic mesenchymal stem cells. Most preferably, the stem cells are autologous mesenchymal stem cells.

Stem cells utilized in the present invention can be collected, established into cell lines, and propagated in vitro by methods including standard methods among those known in the art. Such methods include those disclosed in U.S. Pat. No. 6,355,239, Bruder et al., issued Mar. 12, 2002; and U.S. Pat. No. 6,541,024, Kadiyala et al, issued Apr. 1, 2003. The stem cells of this invention additionally can also be grown in vitro in a culture medium comprising one or more growth factors, such as a growth factor of the transforming growth factor beta (TGF-β) superfamily. In various embodiments, growth factors useful herein include VEGF-1, a fibroblast growth factor (FGF) such as FGF-2, epidermal growth factor (EGF), an insulin-like growth factor-1 (IGF) such as IGF-1 or IGF-II, a transforming growth factor (TGF) such as TGF-, platelet-derived growth factor (PDGF), EGM, and a bone morphogenetic protein (BMP) such as BMP-2, BMP-4, BMP-6 or BMP-7.

The present invention provides methods of modulating a stem cell activity, comprising administering electric stimulation to stem cells. As referred to herein, "modulating" refers to the modification of one or more activities of stem cells by, for example, enhancing or increasing the rate, duration or magnitude of such activities. In various embodiments, the activity is one or more of: increased proliferation, enhanced production of molecules normally produced by the stem cells (such as molecular components of the extracellular matrix, ECM), and accelerated differentiation of stem cells into differentiated cell types. Accelerated differentiation of stem cells includes enhanced production of differentiation markers of differentiated cell types derived from the stem cells, such as, for example, specialized ECM markers, wherein "enhanced production" includes increased and/or accelerated production of such markers, as compared to control stem cells that are not subjected to an electric or electromagnetic field but are otherwise under the same conditions.

Electric Stimulation:

The term "electric stimulation" as used herein includes exposing stem cells to an electric field, such as a direct current electric field, a capacitatively coupled electric field, an electromagnetic field, or combinations thereof. The term "electric stimulation field," as used herein, does not include an electric or electromagnetic field associated with ambient conditions, such as, for example, an electric field generated by casual exposure to radios, telephones, desktop computers or similar devices. Electric stimulation comprises exposing stem cells to an electric or electromagnetic field in vitro, or in situ after implantation into a human or other animal subject in need thereof. In various embodiments, the electromagnetic field is a pulsed electromagnetic field (PEMF). In other embodiments, the stem cells are exposed to electric stimulation in vitro, prior to implantation into a human or other animal subject. In still other embodiments, the stem cells are exposed to electric stimulation in situ, after implantation into the subject.

The strength of the electric field produced during electrical stimulation is preferably at least about 0.5 microvolts per centimeter. In various embodiments, the direct current electric field administered to stem cells has an intensity of at least about 0.5 microamperes, preferably from about 10 to about 200, and preferably from about 20 to about 100 microamperes. Additional embodiments include those wherein the intensity is about 20, about 60, and about 100 microamperes.

The field may be constant, or varying over time. In various embodiments, the field is a temporally varying capacitatively coupled field. In one embodiment, a sinusoidally-varying electric field is used. For example, various embodiments use a sinusoidally-varying electric field for electrodes placed across tissue, such as a site of stem cell implantation in a human patient. Such an implantation site can be a human limb, for example. Preferably, such a sinusoidally-varying electric field has a peak voltage across electrodes placed across the cells of from about 1 volt to about 10 volts, more preferably about 5 volts. In various embodiments, a sinusoidally-varying electric field is produced by electrodes placed across an in vitro culture of stem cells. Preferably, the electric field has peak amplitude of from about 0.1 millivolt per centimeter (mV/cm) to about 100 mV/cm, and more preferably about 20 mV/cm. In various embodiments, the sinusoidal field has a frequency of from about 1,000 Hz to about 200,000 Hz, preferably about 60,000 Hz.

Exposure of stem cells to PEMFs in vitro can be accomplished using methods and apparatuses known in the art for exposure of other cell types to pulsed fields, for example, as disclosed in the following literature: Binderman et al., *Biochimica et Biophysica Acta* 844: 273-279, 1985; Aaron et al, *Journal of Bone and Mineral Research* 4: 227-233, 1989; and Aaron et al., *Journal of Orthopaedic Research* 20: 233-240, 2002. Parameters of cell exposure to an electric stimulation field, such as, for example, pulse duration, pulse intensity, and numbers of pulses, either in vitro or in situ, can be determined by a user. In various embodiments, pulse duration of a PEMF can be from about 10 microseconds per pulse to about 2000 microseconds per pulse, and is preferably about 225 microseconds per pulse. In various embodiments, pulses are comprised in electromagnetic "bursts." A burst can comprise from 1 pulse up to about 200 pulses. Preferably, a burst comprises from about 10 pulses to about 30 pulses, more preferably about 20 pulses, Bursts can be repeated while applying PEMFs to stem cells in vitro or in situ. In still further embodiments, bursts can be repeated at a frequency of from about 1 Hertz (Hz) to about 100 Hz, preferably at a frequency of about 10 Hz to about 20 Hz, more preferably at a frequency of about 15 Hz. In addition, in some preferred embodiments, bursts can repeat at a frequency of about 1.5 Hz, or about 76 Hz. A burst can have a duration from about 10 microseconds up to about 40,000 microseconds; preferably, a burst can have a duration of about 4.5 milliseconds.

An electric field used herein can be produced using any suitable method and apparatus, including such methods and apparatuses known in the art. Suitable apparatus include a capacitatively coupling device such as a SpinalPak® (EBI, L.P., Parsippany, N.J., U.S.A.) or a DC stimulation device such as an SpF® XL IIb spinal fusion stimulator (EBI, L.P.). PEMF can be produced using any known method and apparatus, such as using a single coil or a pair of Helmholtz coils. For example, such an apparatus includes the EBI Bone Healing System® Model 1026 (EBI, L.P.). In various embodiments, the electrical stimulation of implanted stem cells, in vivo, comprises direct current electric field generated using any known device for generating a direct current electric field, such as, for example, an Osteogen™ implantable bone growth stimulator (EBI, L.P., Parsippany, N.J.).

Methods of Treatment:

The present invention provides methods of treating a human or other mammal subject in need thereof, using electrically stimulated stem cells. In one embodiment, such methods comprise providing an in vitro culture comprising stem cells, administering an electric stimulation to the in vitro culture, and implanting the stem cells into the subject. In another embodiment, such methods comprise implanting stem cells into the mammal subject, and administering an electric stimulation to the stem cells in situ. Administration of electrical stimulation "in situ" refers to subjecting stem cells to electrical stimulation after they have been implanted in a human or other mammal subject.

In a preferred embodiment, the present invention provides methods of treating a human or other mammal subject having a tissue defect, using electrically stimulated stem cells that are implanted at the site of the tissue defect. In one embodiment, such methods comprise providing an in vitro culture comprising stem cells, administering an electric stimulation to the in vitro culture, and implanting the stem cells at the site of the defect. In another embodiment, such methods comprise implanting stem cells into the mammal subject at the site of the defect, and administering an electric stimulation to the stem cells in situ. In some embodiments, such implanted stem cells are cultured, such as stem cells treated in vitro by methods of this invention. In other embodiments, implanted stem cells may be obtained by other means, such as by collection and, optionally, isolation and concentration from a human or other animal source. In various embodiments, the stem cells may be autologous, that is, collected from the subject to whom they are to be administered. The stem cells may be isolated and concentrated using a variety of methods, including centrifugation, enzymatic, ultrasonic, and other methods known in the art.

Variations of the aforementioned embodiments include the co-administration of growth factors. In various embodiments, growth factors useful herein include a growth factor of the transforming growth factor beta (TGF-β) superfamily, such as VEGF-1, a fibroblast growth factor (FGF) such as FGF-2, epidermal growth factor (EGF), an insulin-like growth factor-1 (IGF) such as IGF-1 or IGF-II, a transforming growth factor (TGF) such as TGF-, platelet-derived growth factor (PDGF), EGM, and a bone morphogenetic protein (BMP) such as BMP-2, BMP-4, BMP-6 or BMP-7. Without limitation to a specific mechanism of action, in various embodiments administration of electric stimulation potentiates the activity of growth factors that are endogenous at the site of stem cell implantation, co-administered with the stem cells, or both. In various embodiments methods include administering an electric field and a subefficacious amount of growth factor. A "subefficacious amount" of growth factor is an amount of growth factor that is not efficacious in treating a tissue defect by itself.

As referred to herein, such "tissue defects" include any condition involving tissue which is inadequate for physiological or cosmetic purposes. Examples of such defects include those that are congenital, those that result from or are symptomatic of disease, disorder, or trauma, and those that are consequent to surgical or other medical procedures. Embodiments include treatment for vascular, bone, skin, nerve, and organ tissue defects. Examples of such defects include those resulting from osteoporosis, spinal fixation procedures, hip and other joint replacement procedures, chronic wounds, myocardial infarction, fractures, sclerosis of tissues and muscles, Alzheimer's disease, Parkinson's disease, and spinal cord or other nerve injury.

In various embodiments, the compositions and methods of this invention may be used to repair bone or cartilage defects. A preferred embodiment is for the treatment of bone defects. As referred to herein, such "bone defects" include any condition involving skeletal tissue which is inadequate for physiological or cosmetic purposes. Examples of such defects include those that are congenital (including birth defects), those that result from disease, disorder, or trauma, and those that are consequent to surgical or other medical procedures. Examples of such defects include those resulting from bone fractures (such as hip fractures and spinal fractures), osteoporosis, spinal fixation procedures, intervertebral disk degeneration (e.g., herniation), and hip and other joint replacement procedures.

In various embodiments, stem cells are implanted in the culture medium in which they are grown. In other embodiments, stem cells are isolated from the culture medium, and implanted. In further embodiments, pharmaceutically acceptable scaffold for the stem cells is implanted in the human or mammal subject at the site at which the stem cells are implanted. As referred to herein, a "scaffold" is a material that contains or supports stem cells, preferably enabling their growth at the site of implantation. In further embodiments, the stem cells, growth factors, or combinations thereof are mixed with the scaffold material prior to implantation. In still further embodiments, the scaffold material is implanted either before, after, or concurrent with implantation of the stem cells.

Suitable scaffold materials include porous or semi-porous, natural, synthetic or semisynthetic materials. In embodiments for the treatment of a bone defect, a scaffold material can be an osteoconductive material. Scaffold materials include those selected from the group consisting of bone (including cortical and cancellous bone), demineralized bone, ceramics, polymers, and combinations thereof. Ceramics include any of a variety of ceramic materials known in the art for use for implanting in bone, including calcium phosphate (including tricalcium phosphate, tetracalcium phosphate, hydroxyapatite, and mixtures thereof. Polymers include collagen, gelatin, polyglycolic acid, polylactic acid, polypropylenefumarate, and copolymers or combinations thereof. Ceramics useful herein include those described in U.S. Pat. No. 6,323,146 to Pugh et al., issued Nov. 27, 2001, and U.S. Pat. No. 6,585,992 to Pugh et al., issued Jul. 1, 2003. A preferred ceramic is commercially available as ProOsteon™ from Interpore Cross International, Inc. (Irvine, Calif., U.S.A.).

Compositions:

The present invention also provides compositions comprising electrically stimulated stem cells and a pharmaceutically acceptable carrier. Preferably the carrier is a scaffold material as discussed above. Optionally, compositions of this invention additionally comprise one or more growth factors as discussed above, such as a growth factor of the transforming growth factor beta (TGF-β) superfamily.

The following non-limiting examples illustrate the compositions and methods of the present invention.

EXAMPLE 1

In a method for enhancing spinal disc repair, adult autologous or allogeneic mesenchymal stem cells grown in vitro are injected into a degenerating spinal disc in a human patient. An external device providing a capacitatively coupled electric field, or a PEMF, is then worn by the patient. Exposure of the implanted mesenchymal stem cells to an electric or electromagnetic field produced by the device stimulates the stem cells to proliferate and differentiate into nucleus cells and annulus disc cells and also increases extracellular matrix production by those cells, leading to disc repair.

EXAMPLE 2

In a method for healing vertebra after posterolateral spine fusion, bone marrow-derived adult mesenchymal stem cells are mixed with osteoconductive granules comprising a calcium phosphate material such as hydroxyapatite, and implanted into a patient. An implantable direct current stimulator is placed internally in the vicinity of the graft to provide an electric field in situ to enhance bone formation. Bone healing is accelerated through this treatment.

In the above example, noninvasive electrical stimulation is effected using an electric or electromagnetic field generating device to apply capacitatively coupled electric fields or PEMFs, with substantially similar results. Also, in the above example, a composition comprising a scaffold material, such as demineralized bone and/or collagen is implanted with the stem cells, with substantially similar results.

EXAMPLE 3

In a method of this invention, a hip fracture is treated with a stem cell composition of this method. A culture system is used to expand mesenchymal stem cell numbers or generate three-dimensional constructs. In this system, mesenchymal stem cells are derived from muscle, and grown in culture dishes placed between pairs of Helmholtz coils to generate a uniform PEMF. The stem cells are then harvested, and mixed with collagen as a scaffold material. The composition is then implanted at the site of the fracture, thereby accelerating healing of the bone.

In the above example, the stem cells are grown in culture dishes placed within a capacitatively coupled electric field, with substantially similar results. Also in the above example, the stem cells are derived from bone marrow, muscle, fat, umbilical cord blood, or placenta, with substantially similar results. Also in the above example, collagen is replaced with polyglycolic acid or polylactic acid, with substantially similar results.

EXAMPLE 4

In a method of this invention, the differentiation of mesenchymal stem cells is enhanced with PEMF. Human mesenchymal stem cells are plated in culture dishes such as, for example, 10 cm$^2$ culture dishes, and the non-differentiating cultures are grown to near confluence. The cells in the dishes are then stimulated to undergo osteoblast differentiation in the presence or absence of PEMFs. Samples are taken at different times throughout the differentiation process and examined. Day of plating is designated as day −2. At day 0 (2 days later), cells are stimulated down the osteoblast differentiation pathway. Osteoblast differentiation (to mineralization in vitro) is induced with osteoblast medium (Mesenchymal Stem Cell Growth Medium/10% Fetal Bovine Serum/0.1 μM dexamethasone/50 μM ascorbate/10 mM β-glycerophosphate/50 ng/mL BMP-4). Cell numbers and extracts are collected at days 0, 1, 2, 6, 9, 12, 14, 21, and 28 following mineralization stimulus. Some cells are stained for mineralized state, others are used for Western blot, RNA extraction, osteocalcin assays, and alkaline phosphatase assays. The stem cells subjected to PEMF show increased proliferation compared to control stem cells, as evidenced by increased incorporation of $^{32}P$ dCTP, as well as increased differentiation of osteoblasts, as evidenced by increased amounts of osteocalcin and alkaline phosphatase, as well as various osteocalcin mRNAs detected using Northern blot analysis.

EXAMPLE 5

The growth of stem cells is enhanced in a method of this invention. Stem cell cultures of equal cell density are plated in IMDM+10% FBS+1% L-glutamine+1× penicillin/streptomycin+4 ng/mL FGF-2. Cells are seeded in a 6-well plate, at 3600 cells/cm$^2$, for 12 days. Electromagnetic fields are applied for 8 hours per day. Media is changed on days 4, 7, 9 and 11. The electromagnetic field-treated cell cultures show substantially increased cell density compared to control cells.

EXAMPLE 6

In a method of this invention, the increased differentiation of mesenchymal stem cells by PEMF is further enhanced with the addition of growth factor BMP-2. Human mesenchymal stem cells are plated in culture dishes such as, for example, 10 cm$^2$ culture dishes, and the non-differentiating cultures are grown to near confluence. The cells in the dishes are then stimulated to undergo osteoblast differentiation in the presence or absence of PEMFs and with or without addition of growth factor BMP-2, where BMP-2 is added to the medium to make 40 ng/mL. Samples are taken at different times throughout the differentiation process and examined. Day of plating is designated as day −2. At day 0 (2 days later), cells are stimulated down the osteoblast differentiation pathway. Osteoblast differentiation (to mineralization in vitro) is induced with osteoblast medium (Mesenchymal Stem Cell Growth Medium/10% Fetal Bovine Serum/0.1 μM dexamethasone/50 μM ascorbate/10 mM glycerophosphate/50 ng/mL BMP-4). Cell numbers and extracts are collected at days 0, 1, 2, 6, 9, 12, 14, 21, and 28 following mineralization stimulus. Some cells are stained for mineralized state, others are used for Western blot, RNA extraction, osteocalcin assays, and alkaline phosphatase assays. The stem cells subjected to both PEMF and BMP-2 show increased proliferation compared to stem cells subjected to only PEMF or to only BMP-2, as evidenced by increased incorporation of $^{32}P$ dCTP, as well as increased differentiation of osteoblasts, as evidenced by increased amounts of osteocalcin and alkaline phosphatase, as well as various osteocalcin mRNAs detected using Northern blot analysis. Likewise, stem cells treated with only PEMF or stem cells treated with only BMP-2 show increased proliferation compared to control stem cells not subjected to either PEMF or BMP-2.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

What is claimed is:

1. A method of treatment of a human or other mammalian subject having a bone defect in need of enhanced bone formation, comprising:
   collecting and isolating mesenchymal stem cells from said subject,
   implanting the mesenchymal stem cells into the subject at the site of said defect,
   administering an amount of bone morphogenic protein-2 (BMP-2) at the site of said defect to induce differentiation of said mesenchymal stem cells into osteoblasts, and administering an electric stimulation comprising a pulsed electromagnetic field to the mesenchymal stem cells in situ,
   wherein said electric stimulation potentiates the differentiation of said mesenchymal stem cells induced by said amount of BMP-2, forming bone at the site of said defect, with the result being more efficacious than either administering electrical stimulation or BMP-2 independently of one another.

2. The method according to claim 1, further comprising implanting osteoconductive granules at said site.

3. The method according to claim 1, wherein said defect is a bone disease, fracture, wound, injury, birth defect, spinal fusion, defective cartilage, a site of an orthopedic implant, a degenerated or herniated intervertebral disk, site of intervertebral disk replacement, or spinal cord injury.

4. The method according to claim 1, further comprising implanting a scaffold material at said site.

5. The method according to claim 1, wherein the mesenchymal stem cells are concentrated prior to the implanting.

* * * * *